(12) United States Patent
Villen Altamirano et al.

(10) Patent No.: US 8,297,106 B2
(45) Date of Patent: Oct. 30, 2012

(54) GAS CHROMATOGRAPHY SYSTEM AND METHOD

(75) Inventors: Jesus Villen Altamirano, Albacete (ES); Ana Maria Vazquez Molini, Albacete (ES); Raquel Sanchez Santiago, Albacete (ES); Jose Manuel Cortes Simarro, Albacete (ES)

(73) Assignee: Universidad de Castilla-la Mancha, Albacete (ES)

( * ) Notice: Subject to any disclaimer, the term of this patent is extended or adjusted under 35 U.S.C. 154(b) by 909 days.

(21) Appl. No.: 12/086,069

(22) PCT Filed: Mar. 30, 2006

(86) PCT No.: PCT/ES2006/000153
§ 371 (c)(1),
(2), (4) Date: Dec. 4, 2008

(87) PCT Pub. No.: WO2007/068770
PCT Pub. Date: Jun. 21, 2007

(65) Prior Publication Data
US 2009/0217735 A1 Sep. 3, 2009

(30) Foreign Application Priority Data
Dec. 12, 2005 (ES) .................................. 200503046

(51) Int. Cl.
*G01N 30/12* (2006.01)
*G01N 30/84* (2006.01)
(52) U.S. Cl. ..................................... 73/23.41; 73/23.42
(58) Field of Classification Search ................. 73/23.35, 73/23.41, 23.42, 61.52, 61.55, 61.56; 95/89; 96/101, 103–106; 210/198.2, 634, 656, 659; 422/70, 89; 436/161
See application file for complete search history.

(56) References Cited

U.S. PATENT DOCUMENTS

| 3,887,345 | A |   | 6/1975 | Pollock et al. |
| 4,935,145 | A | * | 6/1990 | Cortes et al. ................... 210/656 |
| 5,347,844 | A | * | 9/1994 | Grob et al. ................... 73/23.41 |
| 5,522,988 | A | * | 6/1996 | Cortes et al. ............... 210/198.2 |

(Continued)

FOREIGN PATENT DOCUMENTS

ES   2 152 153   1/2001

(Continued)

OTHER PUBLICATIONS

Perez, M., et al. "On-line Reversed Phase LC-GC by Using the New TOTAD (Through Oven Transfer Adsorption Desorption) Interface: Application to Parathion Residue Analysis." *J. Microcolumn Separations* (1999) 11(8) pp. 582-589.

(Continued)

*Primary Examiner* — Daniel Larkin
(74) *Attorney, Agent, or Firm* — Ladas & Parry LLP

(57) ABSTRACT

The invention relates to a gas chromatography system for the direct coupling of liquid chromatography and gas chromatography or for the introduction of large sample volumes, which is configured to operate selectively in a retention mode. The inventive system includes a tube (2) having a first inlet part (21), a second inlet part (22) and a retention part (3) between said two inlet parts. The system also includes two gas delivery subsystems (6, 7) and a sample introduction conduit (101) which is connected to the first inlet part (21). The system further includes a discharge conduit (9) and a gas chromatography column (300), both of which are connected to the second inlet part (22). The invention also relates to a gas chromatography method.

20 Claims, 4 Drawing Sheets

U.S. PATENT DOCUMENTS

| | | | | |
|---|---|---|---|---|
| 5,672,810 | A | * | 9/1997 | Shibamoto ............... 73/23.25 |
| 5,759,234 | A | * | 6/1998 | Munari et al. ............... 95/14 |
| 6,311,544 | B1 | | 11/2001 | Bertrand |
| 6,402,947 | B1 | | 6/2002 | Altamirano et al. |
| 6,498,042 | B1 | * | 12/2002 | Wilson ..................... 436/174 |
| 6,652,625 | B1 | | 11/2003 | Tipler et al. |

FOREIGN PATENT DOCUMENTS

| | | |
|---|---|---|
| WO | 2005/038450 | 4/2005 |
| WO | 2005/057145 | 6/2005 |

OTHER PUBLICATIONS

Sanchez, R., et al. "Automated multiresidue analysis of pesticides in olive oil by on-line reversed-phase liquid chromatography-gas chromatography using the through oven transfer adsorption-desorption interface." *J. of Chromatography A*, 1029 (2004) pp. 167-172.

Perez, M., et al. "Pesticide Residue Analysis by Off-Line SPE and On-Line Reversed-Phase LC-GC Using the Through-Oven-Transfer Adsorption/Desorption Interface."*Analytical Chemistry* (2000) vol. 72, No. 4, pp. 846-852.

Sanchez, R., et al. "Direct Analysis of Pesticide Residues in Olive Oil by On-Line Reversed Phase Liquid Chromatography-Gas Chromatography Using an Automated Through Oven Transfer Adsorption Desorption (TOTAD) Interface." *J. Agric. Food Chem.* (2003) 51, pp. 6098-6102.

Senorans, F.J., et al. "Simplex Optimization of the Direct Analysis of Free Sterols in Sunflower Oil by On-Line Coupled Reversed Phase Liquid Chromatography-Gas Chromatography."*J. Agric. Food Chem.* (1998) 46, pp. 1022-1026.

Blanch, G.P., et al. "Rapid Analysis of Free Erythrodiol and Uvaol in Olive Oils by Coupled Reversed Phase Liquid Chromatography-Gas Chromatography."*J. Agric..Food Chem.* (1998) 46, pp. 1027-1030.

Grob, Konrad "Development of the transfer techniques for on-line high-performance liquid chromatography-capillary gas chromatography."*Journal of Chromatography A*, 703 (1995) pp. 265-276.

Vreuls, J. J., et al. "Liquid Chromatography Coupled On-Line with Gas Chromatography: State of the Art." *Journal of AOAC International* (1994) vol. 77, No. 2, pp. 306-327.

Alario, J., et al. "Very-Large-Volume Sampling of Water in Gas Chromatography Using the Through Oven Transfer Adsorption Desorption (TOTAD) Interface for Pesticide-Residue Analysis." *Journal of Chromatography Science* (2001) vol. 39, pp. 65-69.

Sanchez, R., et al. "Determination of Organophosphorus and Triazine Pesticides in Olive Oil by On-Line Coupling Reverse-Phase Liquid Chromatography/Gas Chromatography with Nitrogen-Phosphorous . . . " *Journal of AOAC International* (2005) vol. 88, No. 4, pp. 1255-1260.

Mondello, L., et al. "On-Line Microbore High Performance Liquid Chromatography-Capillary Gas Chromatography for Food and Water Analyses. A Review"*J. Microcolumn Separations* (1996) 8(4) pp. 275-310.

* cited by examiner

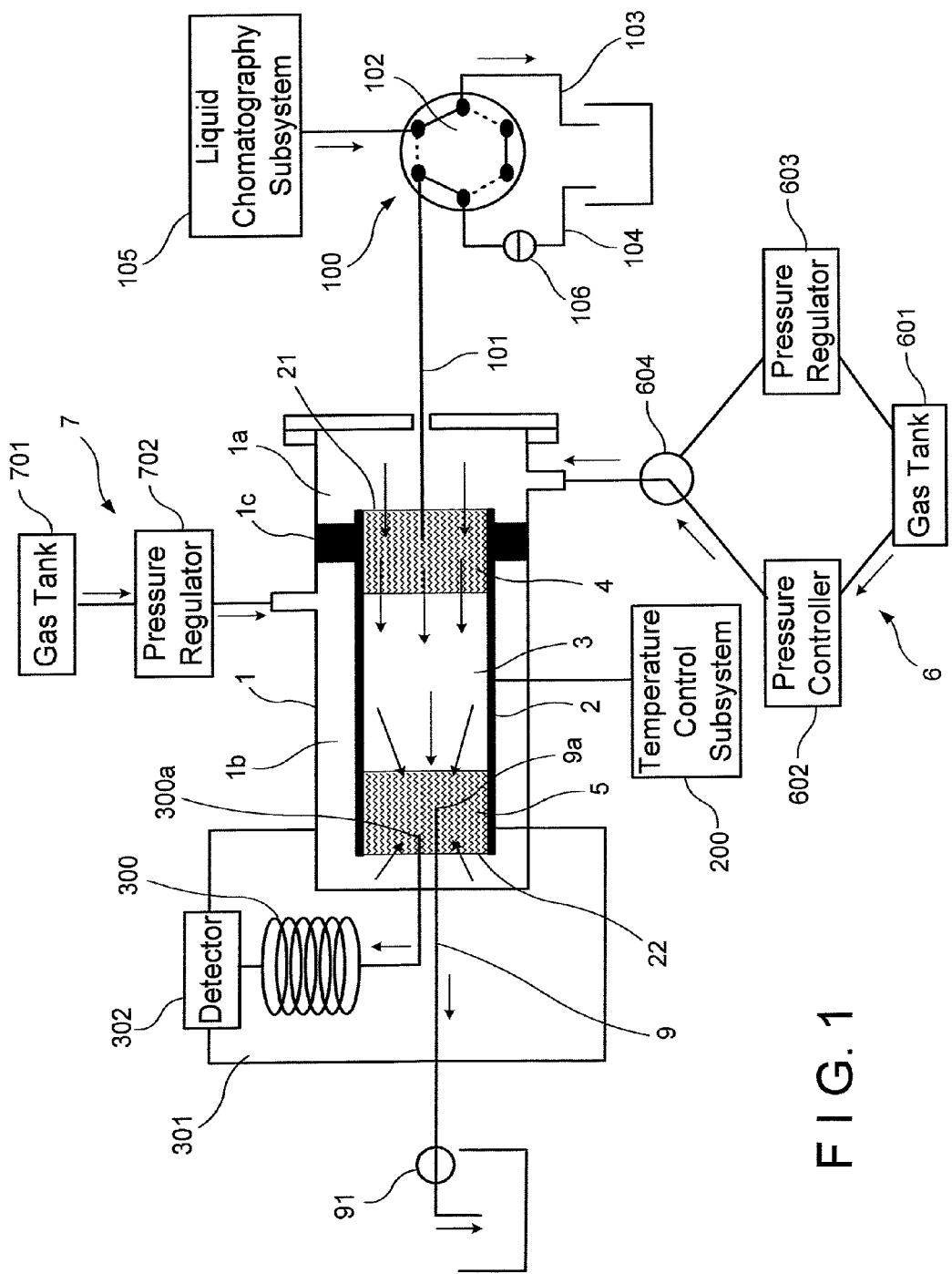
F I G. 1

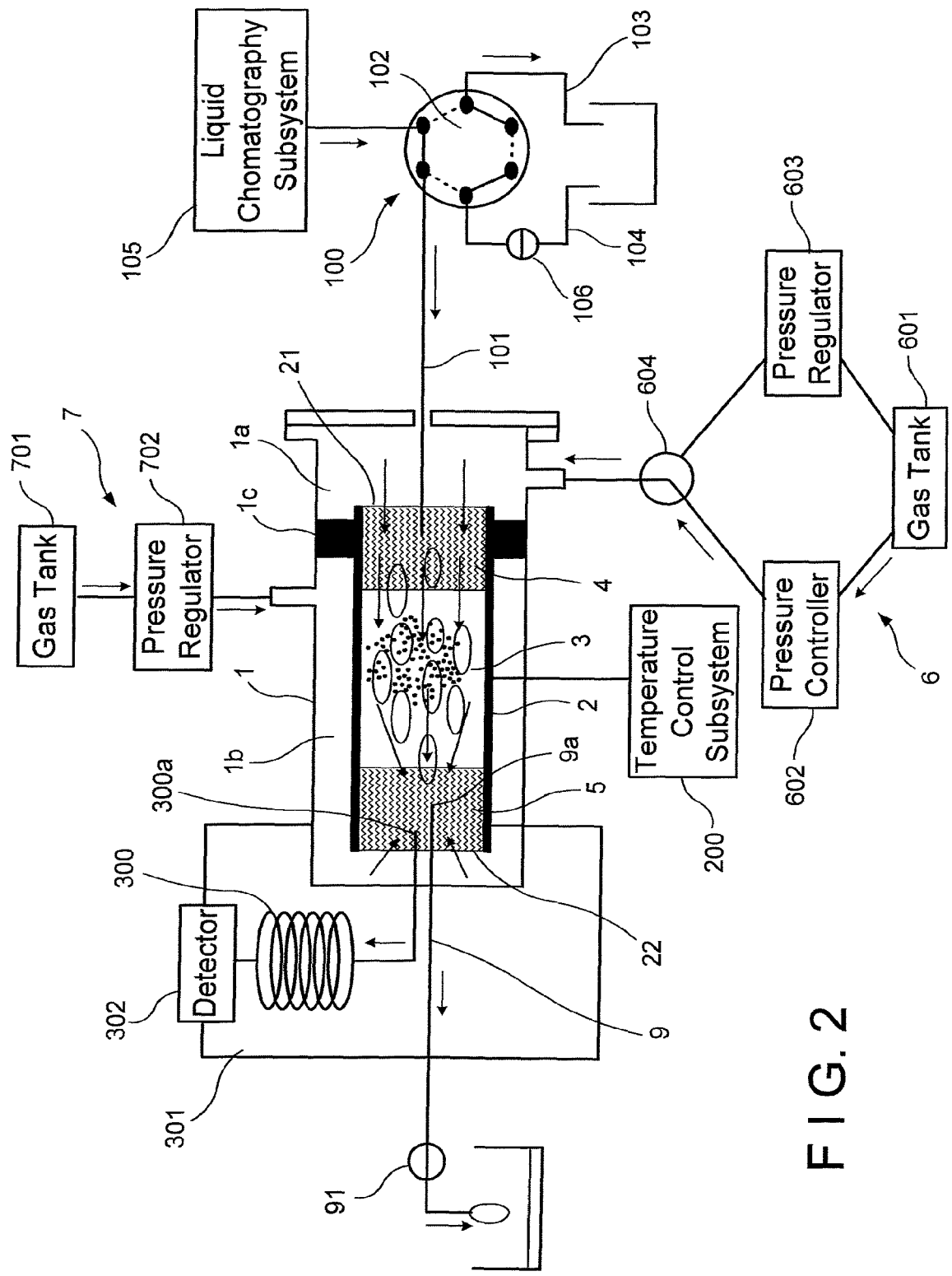
F I G. 2

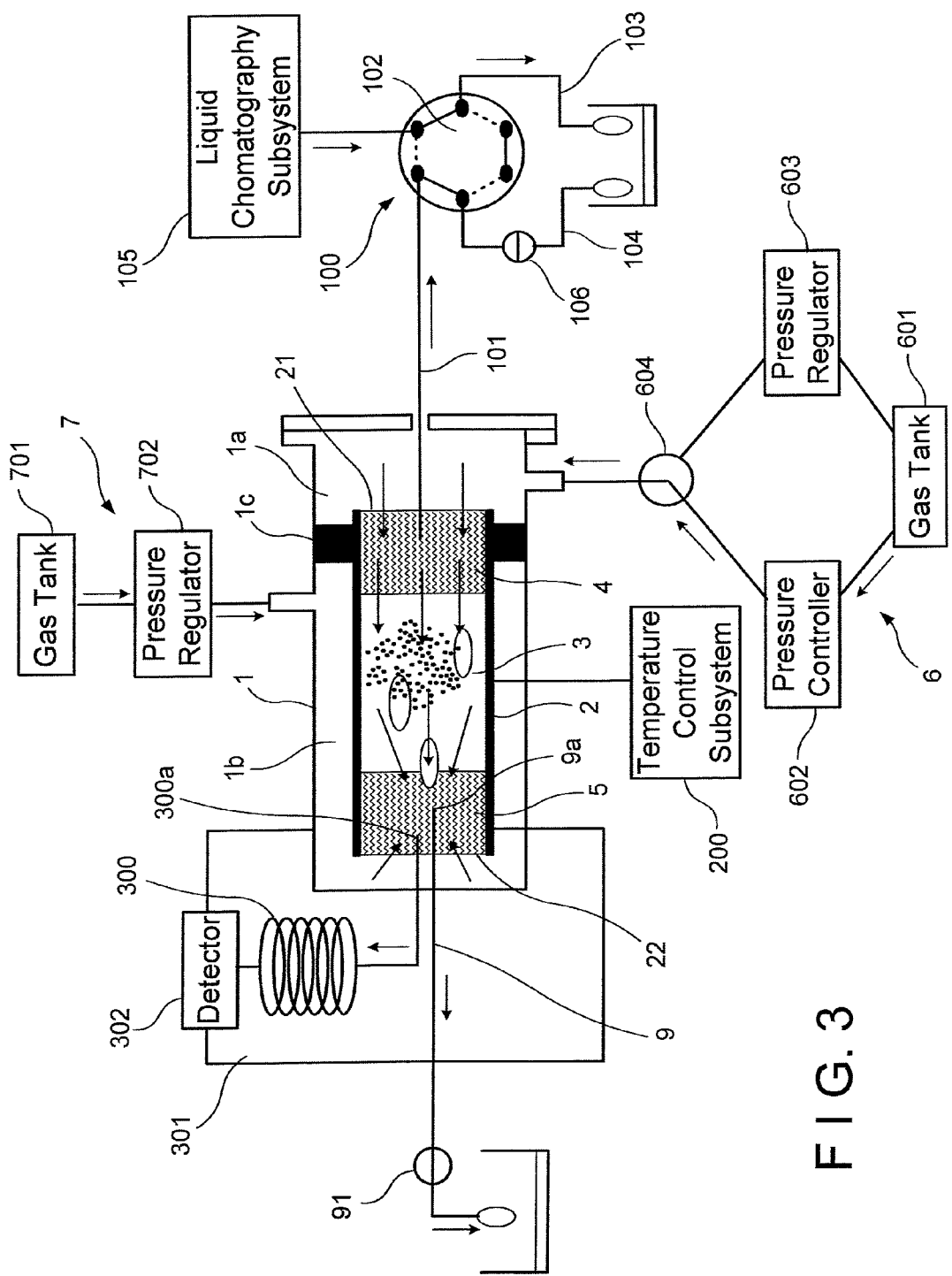
F I G. 3

GAS CHROMATOGRAPHY SYSTEM AND METHOD

TECHNICAL FIELD OF THE INVENTION

The invention is comprised in the field of chromatography.

BACKGROUND OF THE INVENTION

Gas chromatography is an analytical technique which is widely used for analyzing volatile compounds in complex samples, given its high separation power as well as the existence of highly sensitive detectors.

However, a traditional drawback of gas chromatography is that it requires a sample preparation step which is usually laborious and involves the use of large amounts of solvents that are usually toxic for the analyst and hazardous for the environment. This sample preparation step further forms the greatest source of errors in the entire analytical process.

Liquid chromatography is mainly used when the compounds to be analyzed are thermolabile or are not volatile, because it has a lower separation power and the detectors are generally less sensitive. However, compared to gas chromatography, it has the advantage that "dirtier" samples can be analyzed, which allows simplifying or even eliminating the sample preparation step.

The use of the direct coupling of high performance liquid chromatography and gas chromatography is very useful for analyzing complex mixtures. The use of this type of "multidimensional system" allows combining the use of liquid chromatography as a sample preparation technique with the use of gas chromatography to obtain a highly sensitive detection (Grob, K., "On-Line Coupled LC-GC", Hüthig, Heidelberg, Germany, 1991; Mondello, L., Dugo, G., Bartle, K D., "On-line Microbore HPLC-CGC for Food and Water analysis. A Review", Journal of Microcolumn Separations, 1996, 8, 275-310). It is thus possible to have analysis methods that do not require the use of conventional sample preparation processes, which apart from being laborious and not very reliable, have the great drawback of requiring the use of relatively high volumes of contaminating organic solvents. In other words, traditional sample preparation can be substituted with a liquid chromatography step, in which a fluid is generated from which a fraction containing the elements or solutes to be detected/analyzed is selected. This fraction is later subjected to a gas chromatography phase.

A problematic aspect in relation to the use of the direct coupling of liquid chromatography and gas chromatography relates to the features of the interface necessary to make said coupling possible. Two essentially different systems in which the operating parameters are substantially different must be made compatible.

The initially developed interfaces only allowed the use of normal phase in the pre-separation performed by liquid chromatography because the physical and chemical characteristics of the solvents used in normal phase (small vapor volume per unit of liquid volume, low surface tension, etc.) facilitate this coupling.

Different interfaces ("autosampler", "on-column", "loop-type") which allow the direct coupling of normal phase liquid chromatography and gas chromatography have been designed and used (Grob, K., "Development of the Transfer Techniques for On-Line HPLC-CGC", Journal of Chromatography A 1995, 703, 265-76; Vreuls, J. J., de Jong, G. J., Ghijsen, R. T., Brinkman, U. A. Th., "LC Coupled On-Line with GC: State of the Art", Journal of the Association of Official Analytical Chemistry International 1994, 77, 306-27).

However, in many cases it is necessary to turn to the use of reverse phase in the liquid chromatography step in order to achieve a certain separation. In fact, most of the analytical applications in which only liquid chromatography is involved are carried out in reverse phase. Therefore, the extension of the field of applicability of the direct coupling of liquid chromatography and gas chromatography requires the development of suitable interfaces for carrying out direct coupling between reversed-phase liquid chromatography and gas chromatography (Señorans, F. J., Villén, J, Tabera, J., Herraiz, M. "Simplex Optimization of the Direct Analysis of Free Sterols in Sunflower Oil by On-Line Coupled RPLC-GC", Journal of Agricultural and Food Chemistry 1998, 46, 1022-26; Villén, J, Blanch, G. P., Ruiz of the Castillo, M. L., Herraiz, M., "Rapid Analysis of Free Erythrodiol and Uvaol in Olive Oils by Coupled RPLC-GC", Journal of Agricultural and Food Chemistry 1998, 46, 1027-31).

With this aim in mind, several systems have been proposed over the last few years ("retention gap", "concurrent solvent evaporation", "open tubular trap", etc) (Grob, K., "Development of the Transfer Techniques for On-Line HPLC-CGC", Journal of Chromatography A 1995, 703, 265-76; Vreuls, J. J., of Jong, G. J., Ghijsen, R. T., Brinkman, U. A. Th. "LC Coupled On-Line with GC: State of the Art", Journal of the Association of Official Analytical Chemistry International 1994, 77, 306-27) although the limitations involved in using polar eluents (fundamentally the high volumes of vaporization produced during transfer and the difficulty of suitably focusing the chromatographic band) have prevented the development of an interface meeting the required conditions as regards simplicity, reliability, versatility and possibility of automation.

Patent application WO-A-99/061127, corresponding to U.S. Pat. No. 6,402,947-B1, the content of which is included herein as a reference, describes an interface device for the direct coupling of liquid chromatography and gas chromatography, designed based on a basic scheme of a PTV (programmed temperature vaporizer) injector which has been modified so that is can be used for the direct coupling of liquid chromatography in normal phase or reverse phase, and gas chromatography, and for the introduction of high volumes in gas chromatography (i.e. of sample volumes which are greater than those usually introduced in gas chromatography, which allows increasing the sensitivity of the analysis). This interface device comprises an outer body with a first end part, a second end part, an intermediate section between said end parts, and an inner cavity divided into a first inner chamber and a second inner chamber, as well as an inner tube arranged in said inner cavity. The inner tube has a first section arranged in the first inner chamber, a second section arranged in the second inner chamber, the first section ending in a first end with a first opening and the second section ending in a second end, as well as an inner channel for housing an adsorbent material trapped between two inorganic wool "plugs". The second section of the inner tube is communicated with a waste conduit. The injector body also comprises a dividing element surrounding the inner tube and dividing the inner cavity into the first inner chamber and the second inner chamber. The device further comprises a system for selecting a liquid chromatography fraction and leading it to the inner tube by means of a first duct with a free end penetrating into the tube through the first end of the tube, and a first valve connected to the opposite end of the first duct, and a discharge system for discharging the liquid chromatography fraction into the inner tube.

This discharge system is designed to prevent the liquid chromatography fraction from entering the gas chromatography column when the device operates in the adsorption mode, which column communicates with the inner tube by means of a second duct which also penetrates into the inner tube through the first end of said inner tube. To that end, the free end of the first duct ending inside the inner tube is located at a first distance from the adsorbent material, and the free end of the second duct which also penetrates into the inner tube is located at a second distance from the adsorbent material, the second distance being greater than said first distance, whereby the possibility of part of the liquid fraction from the liquid chromatography injected in the inner tube in the adsorption phase entering the second tube, i.e. in the tube corresponding to the gas chromatography column, is reduced. Since the first tube and the second tube are located at the same end of the inner tube, and since the waste tube is located at the second end of the inner tube, the "flow" in the adsorption phase goes from the first end to the second end, whereby, due to the fact that the free end of the second duct is "withdrawn" in an "upstream" direction with respect to the free end of the first duct, it is very difficult for a part of the fraction entering the inner tube from the first tube to pass to the second tube when the system operates in an adsorption phase, as described in WO-A-99/061127 (and U.S. Pat. No. 6,402,947-B1).

The configuration described in WO-A-99/061127 can have several drawbacks, for example as regards the flexibility it offers for analysis equipment designers. The arrangement with the supply duct for supplying the liquid fraction from the liquid chromatography system located at the same end of the inner tube as the gas column represents a certain limitation while designing complete equipment with its hydraulic, pneumatic and electronic components including the heating system and the detector or detectors associated to the gas chromatography column.

In addition, the fact that the transfer capillary traverses the gas chromatograph oven, as described in WO-A-99/061127 (and U.S. Pat. No. 6,402,947-B1), makes it very recommendable for the oven to be maintained at a temperature below the boiling point of the solvents which are transferred to the inner tube during the transfer, as described in the applications developed up until now (Pérez, M., Alario, J., Vázquez, A. and Villén, J., "On-Line Reversed Phase LC-GC by using the New TOTAD (Through Oven Transfer Adsorption Desorption) Interface: Application to Parathion Residue Analysis", Journal of Microcolumn Separations 1999, 11, 582-589; Pérez, M., Alario, J., Vázquez, A. and Villén, J., "Pesticide Residue Analysis by Off-Line SPE and On-Line Reversed Phase LC-GC using the New TOTAD (Through Oven Transfer Adsorption Desorption) Interface", Analytical Chemistry 2000, 72, 846-852; Alario, J., Pérez, M., Vázquez, A. and Villén, J., "Very Large Volume Sampling of Water in GC using the TOTAD (Through Oven Transfer Adsorption Desorption) Interface for Pesticide Residue Analysis", Journal of Chromatography Science 2001, 39, 65-69; Sanchez, R., Vázquez, A. M., Riquelme, D. and Villén, J., "Direct Analysis of Pesticide Residues in Olive Oil by On-Line Reversed Phase Liquid Chromatography-Gas Chromatography using an Automated Through Oven Transfer Adsorption Desorption (TOTAD) Interface", Journal of Agriculture and Food Chemistry 2003, 51, 6098-6102; Sanchez, R., Vázquez, A. M., Andini, J. C. and Villén, J., "Automated Multiresidue Analysis of Pesticides in Olive Oil by On-Line Reversed Phase Liquid Chromatography-Gas Chromatography using the Through Oven Transfer Adsorption Desorption Interface", Journal of Chromatography A 2004, 1029, 167-172; Sanchez, R., Cortés, J. M., Villén, J. and Vázquez, A. M., "Determination of Organophosphorus and Triazine Pesticides in Olive Oil by On-Line Reversed-Phase Liquid Chromatography-Gas Chromatography with a Nitrogen-Phosphorus Detector Using an Automated Through Oven Transfer Adsorption-Desorption Interface", Journal of the Association of Official Analytical Chemistry International 2005, 88, 1255-1260).

Once the transfer is over, it is necessary to heat the gas chromatograph oven until the temperature necessary to start the chromatographic separation and the corresponding analysis, and once the latter has ended, it is necessary to cool the gas chromatograph oven until the temperature that it must have during the transfer. These oven temperature changes involve a time loss (normally from 10 to 15 minutes over a total of 40 to 80 minutes which the analysis lasts, according to the specific application) reducing the capacity of the system to carry out determinations, and which could be prevented if the transfer capillary did not traverse the gas chromatograph oven.

However, this arrangement has been considered necessary to prevent the liquid fraction from passing to the gas chromatography column during the adsorption phase.

DESCRIPTION OF THE INVENTION

A first aspect of the invention relates to a gas chromatography or interface system, configured for the direct coupling of liquid chromatography and gas chromatography, or for the introduction of high sample volumes, configured to work selectively in a retaining mode (which can be an adsorption, absorption or precipitation mode, for example), in which part of the sample (which at least partly comprises an analyte, so as to allow retaining the analyte and evacuating another part of the sample, for example a solvent or part of a solvent forming part of the sample and in which the analyte is dissolved) is retained (for example by adsorption, absorption or precipitation), and in an evaporation mode (in which the matter retained— adsorbed, absorbed or precipitated, for example,—in the retaining mode is recovered in the form of gas).

The system comprises:

a tube (for example, a glass or quartz tube, of the type called "glass-liner", which can have any shape provided that it is not incompatible with the functionality of the device) comprising a retaining part, said tube having at least one first inlet part (which can comprise one or more holes at an end of the tube, or simply an open end of the tube) and one second inlet part (which can comprise one or more holes in another end of the tube, or simply said other open end) located such that the retaining part is located between the first inlet part and the second inlet part, such that a fluid passing from the first inlet part to the second inlet part traverses the retaining part;

a first gas supply subsystem connected to the first inlet part to supply, in a controlled manner (for example, under the control of an electronic control subsystem), a gas (helium, for example) to the first inlet part, such that the gas enters the tube through the first inlet part;

a second gas supply subsystem connected to the second inlet part to supply, in a controlled manner, a gas (helium, for example) to the second inlet part, such that said gas enters the tube through the second inlet part;

at least one sample introduction duct connected to the first inlet part to introduce a sample in the tube through the first inlet part (the sample can comprise at least one solvent and at least one analyte, which can be dissolved in the solvent);

an evacuation duct connected to the second inlet part, to evacuate a part of the sample (for example, the solvent or a substantial part of the solvent, to reduce the volume of the sample, while at the same time the retaining part retains the analyte or analytes or, at least a substantial part of the analyte or analytes; the volume of the sample can thus be "reduced" or it can be "concentrated", which allows, for example, coupling a liquid chromatography system to a gas chromatography system, working with small volumes compared to those of a liquid chromatography system); and at least one gas chromatography column (normally associated to a detector, which can be a conventional detector of the type used for this type of devices).

According to the invention, the gas chromatography column is connected to the second inlet part, to receive a gas from the retaining part of the tube.

This coupling in the second inlet part (i.e., in the inlet part corresponding to the evacuation duct, and not in the first inlet part corresponding to the sample introduction duct for introducing the sample in the tube) has traditionally been considered as unsuitable, given that it would initially be considered that an important part of the solvent could be introduced in the gas chromatography column (or in the ducts leading to said column) instead of passing to the evacuation duct. To that end, the only option considered suitable up until now is placing the gas chromatography column in the inlet part in which the sample introduction duct is located. However, this location of the gas chromatography column has been shown to be problematic from the point of view of flexibility while designing a specific system, as described above. The new location of the gas chromatography column with respect to the tube shows a greater design flexibility, with the advantages that this can involve.

The system can also comprise a temperature control subsystem configured to regulate the temperature of the retaining part, for example, to maintain this part at a first (lower) temperature in the retaining mode and to maintain this part at a second (higher) temperature in the evaporation mode, in order to respectively retain and evaporate one or more analytes contained in a sample passing through the tube.

The system can be configured such that an end of the evacuation duct penetrates in the tube and is located at a first distance from the retaining area, and an end of the gas chromatography column (this end can be an end of a duct joining the actual gas chromatography column with the tube, or an end of the gas chromatography column itself) penetrates in the tube and is located at a second distance from the retaining area, the second distance being greater than the first distance. In this way, and with a suitable operation of the gas supply subsystems in the retaining and evaporation modes, it can be achieved that in the retaining mode, when an evacuation of part of the sample—for example, of the solvent—occurs, the evacuation does not occur through the gas chromatography column, but exclusively or almost exclusively through the evacuation duct.

The system can further comprise a first chamber and a second chamber, with the tube located such that the first inlet part is located in the first chamber and such that the second inlet part is located in the second chamber, and with the first gas supply subsystem connected to the first chamber to supply, in a controlled manner, the gas to the first inlet part through the first chamber, and with the second gas supply subsystem connected to the second chamber to supply, in a controlled manner, the gas to the second inlet part through the second chamber. This configuration facilitates the gas supply to the respective parts of the tube, and provides a basis for a simple and practical construction of the system.

The retaining part can comprise a retaining material, for example, an adsorbent (for example, TENAX®) or absorbent material. The retaining material can be immobilized in the retaining part by means of an inert material, such that a first part of the inert material separates the retaining material from the first inlet part, and a second part of the inert material separates the retaining material from the second inlet part, preventing the retaining material from coming out of said retaining part. The ends of the sample introduction and evacuation ducts, as well as of the gas chromatography column, can be housed in the inert material. The housing of these ducts in the inert material can prevent the gas flow circulating through the tube from causing the movement of this inert material and therefore of the adsorbent or absorbent material. The inert material can comprise inorganic wool, glass wool for example, which has shown to be useful for these applications. The inert material can form two "plugs" at respective ends of the tube, the retaining material (for example, the adsorbent or absorbent material) being housed between these two plugs.

In an alternative configuration, retaining material is not used in the form of plugs, but rather the material of the retaining part can be immobilized by other means, for example, by means of a suitable chemical and/or physical treatment.

The sample introduction duct can be connected to a first valve subsystem (which can include a 4- or 6-way valve for example) to receive the sample through this valve subsystem. The valve subsystem can be configured to selectively introduce a fluid in the sample introduction duct or in a waste duct, and/or the sample introduction duct can be connected, through the valve subsystem, to a liquid chromatography system, to introduce in the tube a sample comprising a fraction of sample obtained in said liquid chromatography system. The suitable fraction can be selected with the valve subsystem such that the unwanted part of what comes from the liquid chromatography system is passed to the waste duct.

The valve system to which the sample introduction duct is connected can be configured such that it allows evacuating the liquid which is located inside said transfer duct.

The sample introduction duct can be connected, through the valve subsystem, to a sample driving system to introduce a liquid sample in the tube.

The evacuation duct can comprise at least one valve, and the system can be configured (in an electronic control unit for example) to open the valve when the system operates in retaining mode, and to close it when the system operates in evaporation mode (to prevent the analytes from passing to the evacuation duct).

The system can comprise an outer body in which the tube is housed, the outer body being divided into the first chamber and the second chamber; the separation may be formed with an inner wall (which can be a graphite cone or VITON ring, for example) acting as a diaphragm and which is traversed by the tube.

The system can be configured such that, in the retaining mode, the first gas supply subsystem introduces the gas towards the inside of the tube through the first inlet part, and such that the second gas supply subsystem introduces the gas towards the inside of the tube through said second inlet part.

The system can be configured such that, in the evaporation mode, the temperature of the retaining part is located at a higher level with respect to the temperature of the retaining part in the retaining mode and the first gas supply subsystem supplies gas towards the inside of the tube through the first inlet part, whereas the second gas supply subsystem does not supply gas in the evaporation mode. This facilitates the introduction of the evaporated analyte in the gas chromatography column.

As suggested above, the system is configured such that the evacuation duct is open in the retaining mode and closed in the evaporation mode.

Another aspect of the invention relates to a gas chromatography method using a system according to that described above. The method comprises the steps of:

a) in a retaining phase, introducing a liquid sample comprising at least one analyte dissolved in a solvent in the tube, through the sample introduction duct, while at the same time gas is supplied to the inside of the tube by means of the first gas supply subsystem and the second gas supply subsystem, such that at least one substantial part (which can be, for example, from close to 100% up to 10% or 5% or even less) of the analyte is retained in the retaining part, and such that at least one substantial part (for example, 99% or more) of the solvent is evacuated through the evacuation duct;

b) in an evaporation phase, evaporating the analyte retained in the retaining part and introducing at least one substantial part of the analyte in the gas chromatography column by means of a gas flow generated by said first gas supply subsystem; and c) carrying out an analysis by gas chromatography of said at least one analyte.

The method can be carried out such that the second gas supply subsystem does not supply gas to the inside of the tube during the evaporation phase.

The evacuation duct can be closed during the evaporation phase.

The sample which is introduced through the sample introduction duct can be obtained from a liquid chromatography system.

The sample which is introduced through the sample introduction duct can be a liquid sample and/or an extract of a sample.

What has been stated with respect to the system is also applicable to the method, *mutatis mutandis* (change as appropriate).

DESCRIPTION OF THE FIGURES

To complement the description and with the aim of aiding to better understand the features of the invention according to a preferred practical embodiment thereof, a set of drawings is attached as an integral part of said description, in which the following has been shown with an illustrative and non-limiting character:

FIG. 1 shows a schematic diagram of the system, in a stabilization phase prior to carrying out an analysis (with the system in retaining mode).

FIG. 2 shows a schematic diagram of the system, in a sample introduction or transfer phase for introducing the sample in the tube (with the system in retaining mode).

FIG. 3 shows a schematic diagram of the system, in a solvent residue elimination phase (with the system in retaining mode).

PREFERRED EMBODIMENT OF THE INVENTION

Figure 4:
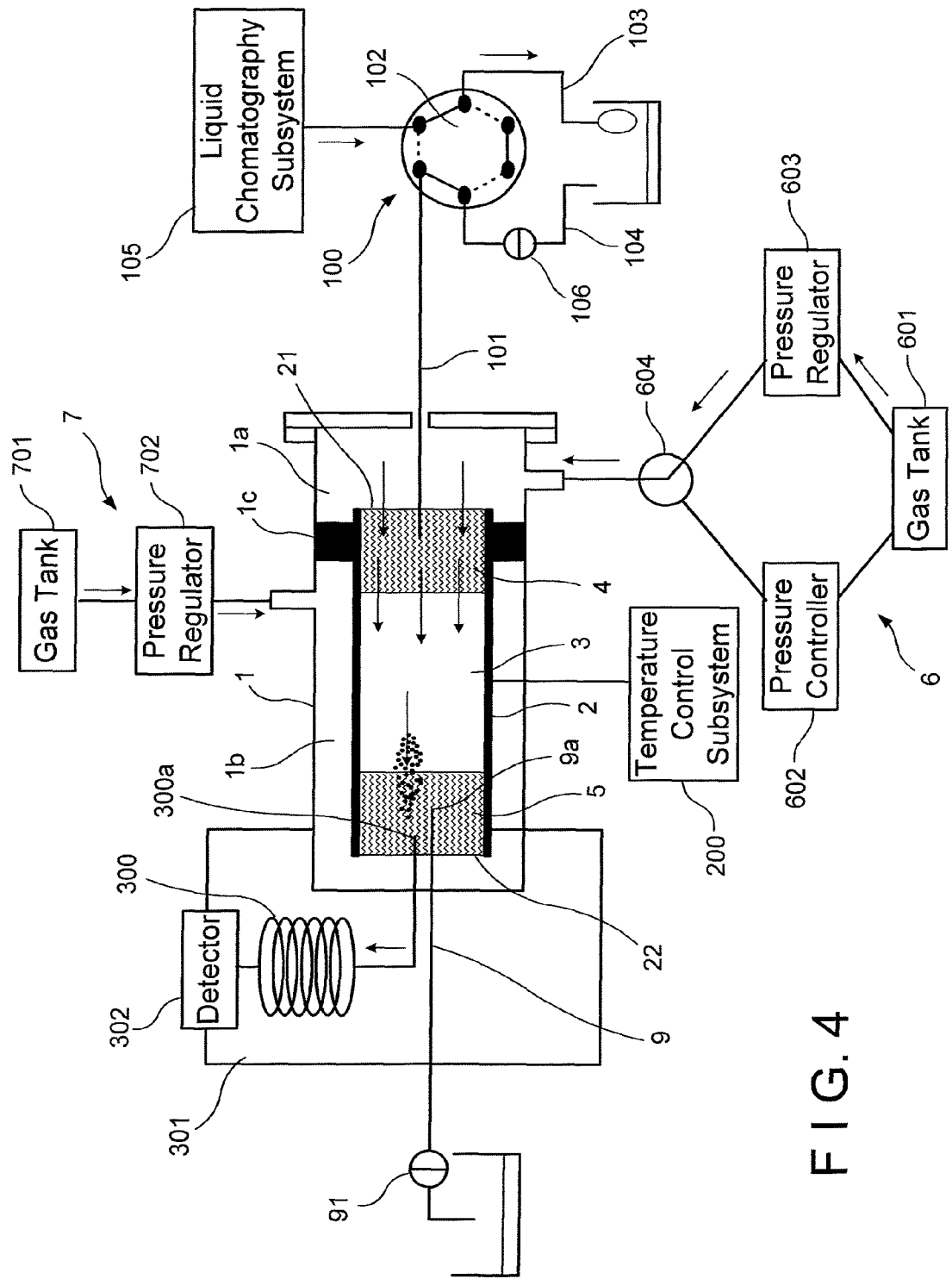
FIG. 4 shows a schematic diagram of the system, in a desorption phase (corresponding to the evaporation mode).

FIG. 1 shows how the system comprises a glass or quartz tube 2 ("glass-liner") with a first inlet part 21 and a second inlet part 22, between which there is a retaining part 3 housing an adsorbent material (for example, TENAX®) retained between two glass wool plugs 4 and 5. The tube is housed in an outer body 1 and traverses an inner wall or diaphragm 1c of the outer body, separating the outer body into a first chamber 1a (in which the first inlet part 21 of the tube is located) and a second chamber 1b (in which the second inlet part 22 of the tube 2 is located).

A temperature control subsystem 200 (which can comprise an electric resistance or the like—and which can also comprise a cooling system which could shorten the necessary times for reaching low temperatures, and/or it could cool until temperatures below room temperature—clasping the retaining part 3 of the tube or located around the outer body 1 or around the second chamber 1b is provided for placing the retaining part 3 of the tube 2 at the suitable temperature in the different operating phases of the system.

In addition, the first chamber is connected to a first gas supply subsystem 6 which can be configured in many ways but in this embodiment of the invention it comprises a pressurized gas tank 601, an electronic flow or pressure controller 602, a pressure regulator (usually called a pressure reducer) 603 and an electrically-operated three-way valve 604 configured to selectively connect one of the two flow or pressure regulating systems to the first chamber, so as to allow it to supply the gas towards said chamber. When the system operates in retaining mode (as it is shown in FIGS. 1, 2 and 3), the valve 604 is located such that the electronic flow or pressure controller 602 supplies the necessary gas flow for this step (although it depends on the specific application, a flow of about 500 mL/min is usual). When the system works in evaporation mode (as it is shown in FIG. 4), the valve 604 is located such that the pressure regulator 603 supplies gas at the necessary pressure so that the suitable gas flow circulates through the gas chromatography column in order to carry out the chromatographic separation (although it depends on the type of column, when capillary columns, the ones that are currently most used, are used, this flow is normally 1 or 2 mL/min).

In addition, there is a second gas supply subsystem 7 comprising a gas tank 701 and an electronic flow or pressure controller 702 connected to supply gas to a the second chamber 1b. The gas tanks 601 and 701 can be one and the same physical tank. In fact, it is even possible that the two gas supply subsystems share valves, flow controllers and/or other constructive elements.

In addition, the system comprises a sample introduction duct 101 traversing an end of the outer body 1 and having an end inserted in the first inlet part 21 of the tube 2 and housed inside one of the glass wool plugs 4. The other end of the duct is joined to a 6-way valve 102 having another of its ports connected to a liquid chromatography system 105 so as to receive a sample from said system. Another two ports of said valve are connected to waste ducts 103 and 104, one of which is provided with an electrically-operated valve 106.

In addition, a gas chromatography column 300, with its corresponding oven 301 and detector device 302 has been provided in correspondence with the other end of the outer body 1. The gas chromatography column 300 has an inlet duct which is inserted in the second inlet part 22 of the tube 2, housed in the corresponding glass wool plug 5. In addition, an evacuation duct 9 is also inserted in said second inlet part 22, the end 9a of which evacuation duct is located closer to the retaining part 3 than the end 300a of the gas chromatography column. The evacuation duct has an electrically-operated valve 91. Both the sample introduction duct 101 and the evacuation duct 9 can be capillary ducts or the like.

The operation of the device can be as follows:

In a first stabilization phase, both the first gas supply subsystem 6 and the second gas supply subsystem 7 are running and supply a gas (such as helium) towards the inside of the tube 2, through the first 1a and second 1b chambers respectively, as indicated in FIG. 1 with the corresponding arrows. The gas flow rate supplied by the system 6 is regulated in this phase by the electronic flow or pressure controller 602, as indicated in FIG. 1. In addition, the sample introduction duct is closed (see the positions of the two valves 102 and 106), and the evacuation duct 9 is open (see the position of the valve 91, which is open). Therefore, the gas traverses the tube (entering through the two ends of the tube) and leaves through the evacuation duct and through the gas chromatography column 300, as indicated by the corresponding arrows in FIG. 1. The temperature of the retaining area is regulated to the temperature necessary for the retention. A liquid or sample is being received from the liquid chromatography column 105, but said sample is expelled through the duct 103 (as indicated by the arrows). With this first phase, the interface reaches the temperature and the gas flows whereby the operation will be carried out in the following transfer step, such that when said following transfer step begins, the interface is at the necessary a stable temperature, and the gases also circulate in stable manner at the time in which liquid starts arriving in the tube, which occurs at the start of the following phase.

In the following phase, which can be called the transfer phase, a sample is transferred to the tube 2. This phase is shown in FIG. 2; with respect to FIG. 1, it can be observed how the position of the 6-way valve has been modified, such that the liquid coming from the liquid chromatography system 105, and corresponding to a "fraction" of the sample treated in said column (and comprising one or more analytes dissolved in a solvent), passes through the sample introduction duct 101, reaching the inside of the tube. The temperature control subsystem 200 maintains the adsorbent material in the retaining part 3 at a temperature, which has been previously stabilized in the previous step, making the analyte or analytes of the sample be retained by adsorption on the surface of the adsorbent material. However, the solvent can continue its path to the evacuation duct 9, driven by the gas stream created by the gas supply system 6, as shown with the corresponding arrows in FIG. 2. The gas stream supplied by the gas supply subsystem 7 penetrates into the tube through the second inlet part 22 and also leaves through the evacuation duct 9, as also indicated with the corresponding arrows in FIG. 2. This gas stream prevents the solvent from being able to reach the end of the gas chromatography column 300. In short, the gas stream makes the solvent reaching the tube 2 (or at least a substantial part of said solvent) be continuously expelled through the duct 9, but due to the difference between the end 9a of the evacuation duct and the end 300a of the gas chromatography column (the end 9a is located closer to the part in which the sample enters the tube 2 than the end 300a), and due to the gas streams entering through both inlet parts 21 and 22 of the tube 2, said solvent does not enter (at least not substantially) the gas chromatography column.

FIG. 3 shows the system in retaining mode and in a solvent residue elimination phase. Here, the 6-way valve has returned to its previous position and the valve 106 has opened, such that the possible liquid which continues to come from the liquid chromatography system is sent to waste through the duct 103, while at the same time the liquid residues in the sample introduction duct 101 are expelled through the duct 104, pushed by the gas, which inside the tube is at a pressure greater than atmospheric pressure. The gas steam continue as in FIG. 2, such that the solvent residues remaining in the tube 2 (or at least a substantial part of said solvent) are expelled through the duct 9.

In FIG. 4, the system is in an a evaporation mode or desorption mode, in which the temperature control subsystem 200 raises the temperature of the adsorbent material, causing the evaporation of the analytes retained in said material. In addition, the valve 91 has closed, therefore no fluid can pass through the evacuation duct 9;

the valve 106 has closed, therefore no fluid can pass through the sample introduction duct 101;

the second gas supply subsystem 7 has closed, therefore gas does not enter through the second chamber 1b anymore; and the position of the valve 604 has changed, such that now the first gas supply subsystem 6 supplies gas through the pressure regulator 603 towards the first chamber 1a.

There is now a gas flow coming from the first inlet part 21 and traversing the adsorbent material 3, entraining the analytes towards the only duct which is open, specifically the duct of the gas chromatography column 300.

The analytes thus pass to said column and can be conventionally analyzed in the detector 302. The pressure regulator 603 regulates the pressure at the head of the chromatographic column so that a suitable gas stream for the chromatographic separation circulates through said column.

The entire "sample preparation" process, which is so laborious in many conventional analytical methods in which gas chromatography is used, is thus made easier.

In this text, the word "comprises" and its variants (such as "comprising", etc.) must not be interpreted in an exclusive manner, i.e., they do not exclude the possibility that what has been described includes other elements, steps, etc.

In addition, the invention is not limited to the specific embodiments which have been described but also includes, for example, the variants which can be carried out by a person having ordinary skill in the art (for example as regards the selection of materials, dimensions, components, configuration, etc.), within that inferred from the claims.

The invention claimed is:

1. A gas chromatography system configured to work selectively in a retaining mode and in an evaporation mode, comprising:

a tube (2) comprising a retaining part (3), said tube (2) having at least one first inlet part (21) and one second inlet part (22) located such that said retaining part (3) is located between said first inlet part (21) and said second inlet part (22) such that a fluid sample passing from said first inlet part (21) to said second inlet part (22) traverses said retaining part (3);

a first gas supply subsystem (6) connected to said first inlet part (21) to supply, in a controlled manner, a gas to said first inlet part, such that said gas enters the tube (2) through said first inlet part (21);

a second gas supply subsystem (7) connected to said second inlet part (22) to supply, in a controlled manner, a gas to said second inlet part (22), such that said gas enters the tube (2) through said second inlet part (22);

at least one sample introduction duct (101) connected to said first inlet part (21) to introduce the sample in the tube (2) through said first inlet part (21);

an evacuation duct (9) connected to said second inlet part (22) to evacuate a part of the sample;

a temperature control subsystem (200) configured to regulate the temperature of the retaining part (3);

the system additionally comprising at least one gas chromatography column (300); wherein said gas chromatography column (300) is connected to said second inlet part (22) to receive a gas coming from the retaining part (3) of the tube (2), and wherein an end (9*a*) of the evacuation duct (9) penetrates into the tube (2) and is located at a first distance from the retaining part (3), and an end (300*a*) of the gas chromatography column (300) penetrates into the tube (2) and is located at a second distance from said retaining area (3), said second distance being greater than said first distance.

2. A system according to claim 1, further comprising a first chamber (1*a*) and a second chamber (1*b*), the tube (2) being located such that said first inlet part (21) is located in said first chamber (1*a*) and such that said second inlet part (22) is located in said second chamber (1*b*), and the first gas supply subsystem (6) being connected to said first chamber (1*a*) to supply, in a controlled manner, the gas to said first inlet part (21) through said first chamber (1*a*), and the second gas supply subsystem (7) being connected to said second chamber (1*b*) to supply, in a controlled manner, the gas to said second inlet part (22) through said second chamber (1*b*).

3. A system according to claim 1, wherein the retaining part (3) comprises a retaining material.

4. A system according to claim 3, wherein said retaining material is an adsorbent material.

5. A system according to claim 3, wherein said retaining material is an absorbent material.

6. A system according to claim 3, wherein the retaining material is immobilized in said retaining part (3) by means of an inert material, such that a first part (4) of said inert material separates the retaining material from the first inlet part (21), and a second part (5) of said inert material separates the retaining material from said second inlet part (22), preventing the retaining material from coming out of said retaining part (3).

7. A system according to claim 2, further comprising an outer body (1) in which the tube (2) is housed, said outer body being divided into said first chamber (1*a*) and second chamber (1*b*).

8. A system according to claim 1, wherein the at least one sample introduction duct (101) is connected to a first valve subsystem (100) to receive the sample through said valve subsystem (100).

9. A system according to claim 8, wherein said valve subsystem (100) is configured to selectively introduce a fluid into the at least one sample introduction duct (101) or in a waste duct (103).

10. A system according to claim 8, wherein the sample introduction duct is connected, through said valve subsystem (100), to a liquid chromatography system (105) to introduce, into the tube (2), a sample comprising a fraction of sample obtained in said liquid chromatography system.

11. A system according to claim 8, wherein the at least one sample introduction duct is connected, through said valve subsystem (100), to a sample driving system to introduce a liquid sample into the tube (2).

12. A system according to claim 1, wherein the evacuation duct comprises at least one valve (91).

13. A system according to claim 1, wherein the tube (2) is a glass or quartz tube.

14. A system according to claim 1, which is configured such that in the retaining mode, the first gas supply subsystem (6) supplies the gas towards an inside of the tube (2) through the first inlet part (21), and the second gas supply subsystem (7) supplies the gas towards the inside of the tube (2) through said second inlet part (22).

15. A system according to claim 14, wherein the evacuation duct (9) is open in the retaining mode and closed in the evaporation mode.

16. A subsystem according to claim 1, which is configured such that in the evaporation mode, the temperature of the retaining part (3) is located at a higher level with respect to the temperature of said retaining part (3) in the retaining mode, and the first gas supply subsystem (6) supplies gas towards the inside of the tube (2) through said first inlet part (21), whereas said second gas supply system (7) does not supply gas in said evaporation mode.

17. A gas chromatography method using a system according to claim 1, comprising the steps of:

a) in a retaining phase, introducing a liquid sample comprising at least one analyte dissolved in a solvent in the tube, through the at least one sample introduction duct (101), while at the same time gas is supplied to the inside of the tube (2) by means of said first gas supply subsystem (6) and said second gas supply subsystem (7), such that at least one substantial part of the analyte is retained in the retaining part (3), and such that at least one substantial part of the solvent is evacuated through the evacuation duct (9);

b) in an evaporation phase, evaporating the analyte retained in the retaining part and introducing at least one substantial part of the analyte in the gas chromatography column by means of a gas flow generated by said first gas supply subsystem (6); and c) carrying out an analysis by gas chromatography of said at least one analyte.

18. A method according to claim 17, wherein the second gas supply subsystem (7) does not supply gas to the inside of the tube (2) during the evaporation phase.

19. A method according to claim 17, wherein the evacuation duct (9) is closed during the evaporation phase.

20. A method according to claim 17, wherein the sample which is introduced through the at least one sample introduction duct (101) is obtained from a liquid chromatography system (105).

\* \* \* \* \*